United States Patent [19]

Gray et al.

[11] Patent Number: 5,089,506

[45] Date of Patent: Feb. 18, 1992

[54] ETHANOBICYCLIC AMINE DERIVATIVES FOR CNS DISORDERS

[75] Inventors: Nancy M. Gray, Ellisville; Brian K. Cheng, St. Charles, both of Mo.

[73] Assignee: G. D. Searle & Co., Chicago, Ill.

[21] Appl. No.: 516,364

[22] Filed: Apr. 30, 1990

[51] Int. Cl.$^5$ .................. A61K 31/445; A61K 31/495; C07D 211/06; C07D 295/00

[52] U.S. Cl. .................................... 514/325; 514/255; 544/403; 546/203; 546/204

[58] Field of Search .................. 546/203, 204; 514/325

[56] References Cited

U.S. PATENT DOCUMENTS 3,821,249  6/1974  Malen et al. ...................... 540/551

FOREIGN PATENT DOCUMENTS 706262  1/1970  Belgium .

OTHER PUBLICATIONS

A. F. Gilman et al., *The Pharmacological Basis of Therapeutics* 7th Edn., p. 403 (1985).
S. M. Rothman et al., *Annals of Neurology*, 19(2), 105-111 (1986).
C. Carter et al., *J. Pharm Exp. Ther.*, 247(3), 1222-1232 (1988).
R. M. Bartholow et al., *J. Pharm. Exp. Ther.*, 202(3) 532-543 (1977).
S. M. Knepper et al., *J. Pharmacol. Exp. Ther.*, 247(2), 487-494 (1988).
H. E. Katerinopoulos et al., *Eur. J. Med. Chem.*, 23(4), 391-396 (1988).

*Primary Examiner*—Cecilia Shen
*Attorney, Agent, or Firm*—J. Timothy Keane; Paul D. Matukaitis

[57] ABSTRACT

Certain ethanobicyclic amine compounds are described for treatment of CNS disorders such as psychotic disorders, convulsions, dystonia and cerebral ischemia. Compounds of particular interest are of the formula

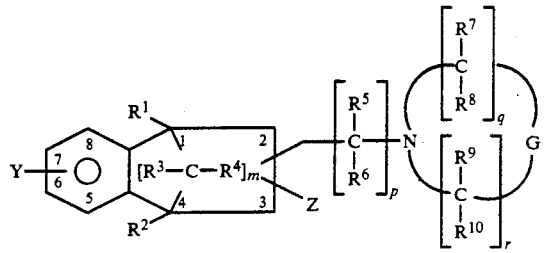

wherein each of $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo;

wherein each of $R^5$, $R^6$, $R^7$, $R^8$, $R^9$ and $R^{10}$ is independently selected from hydrido, alkyl, cycloalkyl, hydroxyalkyl, fluoroalkyl, cycloalkylalkyl, alkoxyalkyl, phenalkyl and phenyl; wherein G within the nitrogen-containing cyclohetero moiety is selected from

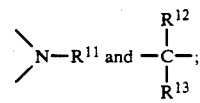

wherein $R^{11}$ is selected from hydrido, alkyl, cycloalkyl, cycloalkylalkyl, phenyl, phenalkyl, alkoxyalkyl and hydroxyalkyl wherein each of $R^{12}$ and $R^{13}$ is independently selected from hydrido, hydroxy, alkyl, phenalkyl, phenyl, alkoxy, fluoroalkyl and fluoro; wherein m is one or two; wherein p is a number selected from zero through four, inclusive; wherein each of q and r is a number independently selected from one through three, inclusive, with the proviso that sum of q and r is a number from three through six, inclusive; with the further proviso that the nitrogen-containing cyclohetero moiety must be attached at one position selected from $R^3$, $R^4$, ring-position two, and ring-position three; or the pharmaceutically-acceptable salts thereof.

13 Claims, No Drawings

ETHANOBICYCLIC AMINE DERIVATIVES FOR CNS DISORDERS

FIELD OF THE INVENTION

This invention is in the field of clinical neurology and relates to a class of compounds, compositions and methods useful for treatment of Central Nervous System (CNS) dysfunctions. Of particular interest is a class of ethanobicyclic amine derivatives useful as antipsychotics, as anticonvulsives, as antiischemic agents and to treat dystonic disorders.

BACKGROUND OF THE INVENTION

There are many classes of compounds known for treatment of psychotic disorders. For example, current therapeutic treatments for psychoses use compounds classifiable as tricyclic-type phenothiazine-thioxanthenes, as phenylbutylpiperidines and also as alkaloids. An example of a piperazine-substituted tricyclic compound of current use in psychotic treatment therapy is fluphenazine [A. F. Gilman et al, *The Pharmacological Basis of Therapeutics*, 7th Edn., p. 403 MacMillan (1985)].

Tricyclic compounds have been investigated for various CNS uses. For example, Belgian Patent No.706,262 describes a class of diphenylenemethane amine and amide derivatives mentioned for use as anticonvulsants, as well as for antidepressive, antiinflammatory and analgesic uses, and mentions in particular the compound 2-[fluorene-9-yl)amino]-acetamide. U.S. Pat. No. 3,821,249 describes a series of dibenzothiazepin derivatives asserted to possess psychostimulant, antidepressive, analgesic, antitussive, antihistaminic and gastric anti-secretory properties, such series including certain specific 7-[dibenzo(a,d) cycloheptadien-5-yl]aminoheptanoic acid derivatives and certain specific 7-[chlorodibenzo(b,e)thiepin-11-yl]aminoheptanoic acid derivatives.

It has been shown that the sensitivity of central neurons to hypoxia and ischemia can be reduced by either blockage of synaptic transmission or by the specific antagonism of postsynaptic glutamate receptors [see S. M. Rothman et al, *Annals of Neurology*, 19(2), 105–111 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

It is known that compounds of various structures, such aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)piperidinyl]ethanol, which are known anti-ischemic agents, have been found to be non-competitive NMDA receptor antagonists [C. Carter et al, *J. Pharm Exp. Ther.*, 247(3), 1222-1232 (1988)].

Other families of bridged bicyclic or tricyclic amine compounds have been investigated for CNS-related purposes. For example, certain primary and secondary benzobicyclo -[2.2.2]octeneamine compounds have been studied as uptake inhibitors of central catecholamines [R. M. Bartholow et al, *J. Pharm. Exp. Ther.*, 202(3), 532-543 (1977)]. U.S. Pat. No. 4,801,753 describes a family of 4-aminobenzo (b)bicyclo[3.3.1]nonene derivatives as antidepressant agents. The compound [1S-(1α,2α,4α)]-1,2,3,4-tetrahydro-1,4-methanonaphthalen-2-amine has been studied as an inhibitor of norepinephrine transport into synaptic vesicles [S. M. Knepper et al, *J. Pharmacol. Exp. Ther.*, 247(2), 487–494 (1988)]. The compound (1α,2α,4α)-1,2,3,4-tetrahydro-2-(propylamino)-1,4-methanonaphthalene-6,7-diol has been investigated for dopamine receptor binding affinity [H. E. Katerinopoulos et al, *Eur. J. Med. Chem.*, 23(4), 391-396 (1988)].

DESCRIPTION OF THE INVENTION

Treatment of CNS disorders and diseases such as psychotic disorders, convulsions, cerebral ischemia and dystonic disorders, may be accomplished by administration of a therapeutically-effective amount of a compound of Formula I:

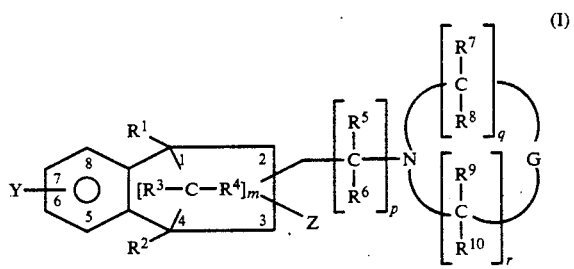

wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkoxycarbonyl, alkenyl and alkynyl; wherein $R^3$ and $R^4$ may be taken together to form oxo; wherein each of $R^5$, $R^6$, $R^7$, $R^8$, $R^9$, and $R^{10}$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein $R^7$ and $R^8$ may be taken together to form oxo; wherein $R^9$ and $R^{10}$ may be taken together to form oxo; wherein G within the nitrogen-containing cyclohetero moiety is selected from

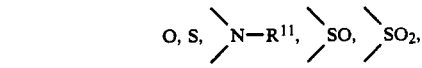

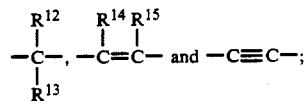

wherein each of $R^{11}$, $R^{14}$ and $R^{15}$ is independently selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein each of $R^{12}$ and $R^{13}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkoxycarbonyl and alkanoyl; wherein $R^{12}$ and $R^{13}$ may be taken together to form oxo;

wherein m is one or two; wherein p is a number selected from zero through four, inclusive, wherein each of q and r is a number independently selected from one through five, inclusive, with the proviso that sum of q and r is a number from three through ten, inclusive; with the further proviso that the said nitrogen-containing cyclohetero moiety must be attached at one position selected from $R^3$, $R^4$, ring-position two and ring-position three; or the pharmaceutically-acceptable salts thereof.

A preferred class of compounds consists of those compounds within Formula I wherein each of $R^1$, $R^2$, $R^3$, $R^4$, Y and Z is independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, carboxy, carboxyalkyl, alkanoyl, alkoxycarbonyl, alkenyl and alkynyl; wherein $R^3$ and $R^4$ may be taken together to form oxo; wherein each of $R^5$, $R^6$, $R^7$, $R^8$, $R^9$, and $R^{10}$ is independently selected from hydrido, alkyl, cycloalkyl, hydroxyalkyl, fluoroalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl and carboxy; wherein G within the nitrogen-containing cyclohetero moiety is selected from

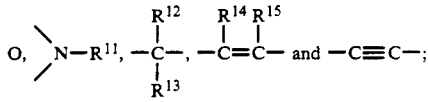

wherein each of $R^{11}$, $R^{14}$ and $R^{15}$ is independently selected from hydrido, alkyl, cycloalkyl, cycloalkylalkyl, aryl, aralkyl, heteroaryl, alkoxyalkyl, hydroxyalkyl, alkanoyl, aralkanoyl and aroyl; wherein each of $R^{12}$ and $R^{13}$ is independently selected from hydrido, hydroxy, alkyl, cycloalkyl, cycloalkylalkyl, aralkyl, aryl, alkoxy, aralkoxy, aryloxy, alkoxyalkyl, fluoroalkyl, hydroxyalkyl, fluoro, alkoxycarbonyl and alkanoyl; wherein m is one or two; wherein p is a number selected from zero through four, inclusive, wherein each of q and r is a number independently selected from one through five, inclusive, with the proviso that sum of q and r is a number from three through six, inclusive; with the further proviso that the said nitrogen-containing cyclohetero moiety must be attached at one position selected from $R^3$, $R^4$, ring-position two and ring position three; or the pharmaceutically-acceptable salts thereof.

A more preferred class of compounds of consists of those cyclic amine compounds of Formula I; wherein each of $R^1$, $R^2$, $R^3$, $R^4$, Y and Z is independently selected from hydrido, hydroxy, alkyl, cycloalkyl, cycloalkylalkyl, phenalkyl, phenyl, alkoxy, phenoxy, phenalkoxy, alkoxyalkyl, halo, haloalkyl and hydroxyalkyl; wherein $R^3$ and $R^4$ may be taken together to form oxo; wherein each of $R^5$, $R^6$, $R^7$, $R^8$, $R^9$ and $R^{10}$ is independently selected from hydrido, alkyl, cycloalkyl, hydroxyalkyl, fluoroalkyl, cycloalkylalkyl, alkoxyalkyl, phenalkyl and phenyl; wherein G within the nitrogen-containing cyclohetero moiety of Formula I is selected from

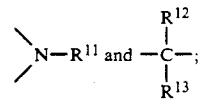

wherein $R^{11}$ is selected from hydrido, alkyl, cycloalkyl, cycloalkylalkyl, phenyl, phenalkyl, alkoxyalkyl and hydroxyalkyl; wherein each of $R^{12}$ and $R^{13}$ is independently selected from hydrido, hydroxy, alkyl, phenalkyl, phenyl, alkoxy, fluoroalkyl and fluoro; wherein m isone or two; wherein p is a number selected from zero through four, inclusive; wherein each of q and r is a number independently selected from one through three, inclusive, with the proviso that sum of q and r is a number from three through six, inclusive; with the further proviso that said nitrogen-containing cyclohetero moiety must be attached at one position selected from $R^3$, $R^4$, ring-position two and ring-position three; or the pharmaceutically-acceptable salts thereof.

Within the class of more preferred compounds of Formula I is a more preferred sub-class of piperidine compounds of Formula II:

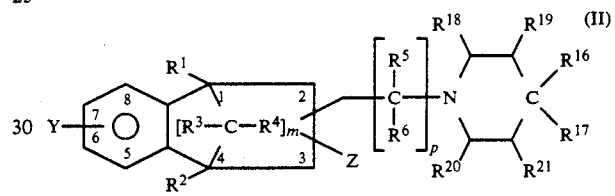

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^5$ and $R^6$ is independently selected from hydrido, alkyl, fluoroalkyl, benzyl and phenyl; wherein each of $R^{16}$ through $R^{21}$ is independently selected from hydrido, hydroxy, alkyl, benzyl, phenyl, alkoxy, fluoroalkyl and fluoro; wherein m is one or two; wherein p is zero or one; or a pharmaceutically-acceptable salt thereof.

An even more preferred class of piperidine compounds of Formula II are those compounds wherein each of $R^1$, $R^2$, $R^3$, $R^4$, Y and Z is independently selected from hydrido, alkyl, halo and haloalkyl; wherein each of $R^5$, $R^6$ and $R^{16}$ through $R^{21}$ is independently selected from hydrido, alkyl, benzyl and phenyl; wherein m one or two; wherein p is zero or one; or a pharmaceutically-acceptable salt thereof.

Especially preferred compounds within Formula II are the compounds 1-(2-benzobicyclo[2.2.2]octenyl)methylpiperidine; 1-(2-benzobicyclo[2.2.2]octenyl)piperidine; 1-(2-benzobicyclo[2.2.1]heptenyl)methylpiperidine; and 1-(2-benzobicyclo[2.2.1]heptenyl)piperidine Another more preferred sub-class of preferred cyclic amines within Formula I consists of those piperazine compounds of Formula III

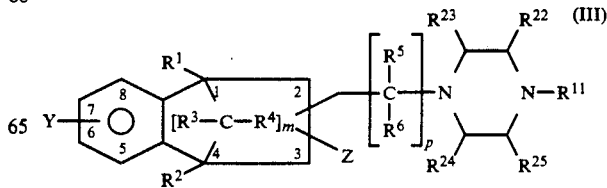

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^5$ and $R^6$ is independently selected from hydrido, alkyl, fluoroalkyl, benzyl and phenyl; wherein $R^{11}$ is selected from hydrido, alkyl, phenyl, benzyl, alkoxyalkyl and hydroxyalkyl; wherein each of $R^{22}$ through $R^{25}$ is independently selected from hydrido, alkyl, benzyl, phenyl, alkoxy and fluoroalkyl; wherein m is one or two; wherein p is zero or one; or the pharmaceutically-acceptable salts thereof.

An even more preferred group of piperazine compounds within Formula III consists those compounds wherein each of $R^1$, $R^2$, $R^3$, $R^4$, Y and Z is independently selected from hydrido, alkyl, halo and haloalkyl; wherein $R^{11}$ is selected from hydrido, alkyl, phenyl, benzyl and hydroxyalkyl; wherein each of $R^5$, $R^6$ and $R^{22}$ through $R^{25}$ is independently selected from hydrido, alkyl, benzyl and phenyl; wherein m is one or two; Wherein p is zero or one; or a pharmaceutically-acceptable salt thereof.

Especially-preferred piperazine compounds of Formula III are the compounds 1-(2-benzobicyclo[2.2.2]octenyl)methyl-4-methylpiperazine; 1-(2 benzobicyclo[2.2.2]octenyl)-4-methylpiperazine; 1-(2-benzobicyclo[2.2.1]heptenyl)methyl-4-methylpiperazine; and 1-(2-benzobicyclo[2.2.1]heptenyl)-4-methylpiperazine.

The phrase "therapeutically-effective amount" means that amount of one or more compounds of Formula I-III which provides a therapeutic benefit in treatment or management of a CNS disorder or a neurodegenerative disease. A "therapeutically-effective amount" of a compound of Formula I would be an amount of the compound which is effective to treat a psychotic disorder, a convulsive disorder or a dystonic disorder. In cases of treatment of a neurodegenerative disease, the amount of a "therapeutically-effective amount" of a compound of Formula I would be that amount effective to reduce or prevent neurodegeneration arising from or causing CNS disorders such as convulsions, stroke and epilepsy.

The term "hydrido" denotes a single hydrogen atom (H) which may be attached, for example, to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to ten carbon atoms, such as cyclopropyl, cyclobutyl, cyclohexyl and cycloheptyl. An example of "cycloalkylalkyl" is cyclohexylmethyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy" embraces linear or branched oxy-containing radicals having an alkyl portion of one to about ten carbon atoms, such as methoxy, ethoxy, isopropoxy and butoxy. An example of "cycloalkyloxy" is cyclohexyloxy. An example of "alkoxyalkyl" is methoxymethyl. An example of "aralkyloxy" is benzyloxy. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals $>SO$ and $>SO_2$. The terms "monoalkylamino" and "dialkylamino" denote amino groups which have been substituted, respectively, with one alkyl radical and with two alkyl radicals. The term "acyl" whether used alone, or within a term such as acyloxy, denotes a radical provided by the residue after removal of hydroxyl from an organic acid, examples of such radical being acetyl and benzoyl.

Within this class of compounds of Formulas I to III are the tautomeric forms of the described compounds, isomeric forms including diastereoisomers and the pharmaceutically-acceptable salts of such compounds. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxy-ethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. Mixtures of these resulting diastereoisomers may be separated by crystallization followed by liberation of the optically active bases from these salts. A different process for separation of optical isomers involves the use of achiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

General Synthetic Procedures

Compounds of Formulas I-III may be prepared in accordance with the following general procedures:

Generic Procedure 1

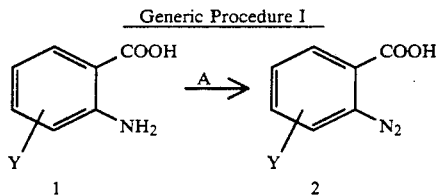

wherein Y is as defined before; wherein A can be a variety of nitrite reagents such as sodium nitrite, isoamyl nitrite or amyl nitrite.

One of the process that can be used to synthesize the products of the invention starts with anthranilates of general structure 1 where Y has the value assigned previously. The anthranilate is treated with the nitrite reagent A in the presence of a catalytic amount of Bronsted acids like hydrochloric acid, trifluoroacetic acid or sulfuric acid to generate the diazonium salt of general structure 2. The reaction is best achieved by mixing the reagents in a solvent like water, tetrahydrofuran or ether. The temperature of the reaction can vary from about −15° C. to room temperature.

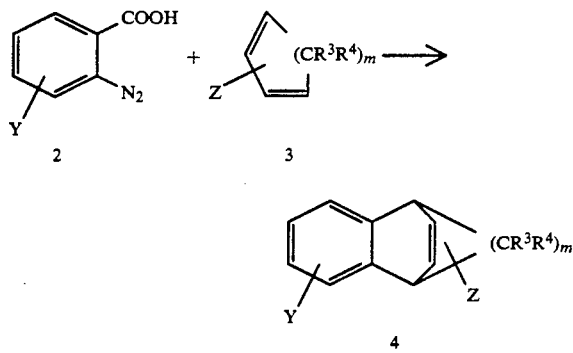

wherein m, $R^3$, $R^4$, Y and Z are as defined previously.

In the second step of the process, the diazonium salt 2 is transformed into the bicyclic compound 4 by mixing with the diene 3 where m, $R^3$, $R^4$ and Z have the values assigned previously. The reagents are combined in a solvent such as ether or tetrahydrofuran. The reaction temperature may vary from room temperature to reflux of the reaction mixture.

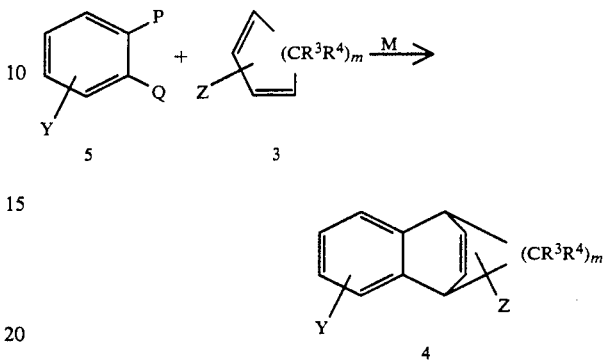

wherein m, $R^3$, $R^4$, Y and Z are as defined previously; wherein P and Q are halogens selected from fluoro, chloro, bromo or iodo; wherein M is a metal such as magnesium.

Alternately, the bicylic compound 4 can be prepared by combining the diene 3 with the dihaloaryl 5, where P and Q are halogens selected from fluoro, chloro, bromo, or iodo, and with a metal such as magnesium. The reagents are combined in a solvent such as ether, tetrahydrofuran, or diglyme. The temperature of the reaction may vary from room temperature to reflux of the reaction mixture.

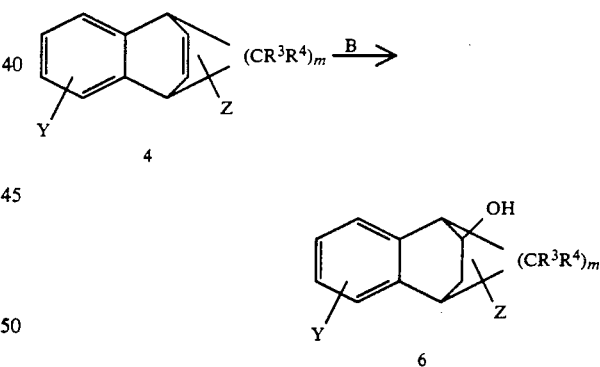

wherein m, $R^3$, $R^4$, Y and Z are as defined previously; wherein B represents reagents such as mercuric acetate and sodium borohydride or diborane and hydrogen peroxide.

In the third step of the process, the bicyclic compound 4 can be converted to the alcohol 6 by reaction with a variety of reagents B, such as mercuric acetate and sodium borohydride, diborane and hydrogen peroxide, or other reagents familiar to those skilled in the art. The reagents are combined in the proper order in a solvent such as tetrahydrofuran or ether and the reaction temperature may vary from about 0° C. to reflux of the reaction mixture.

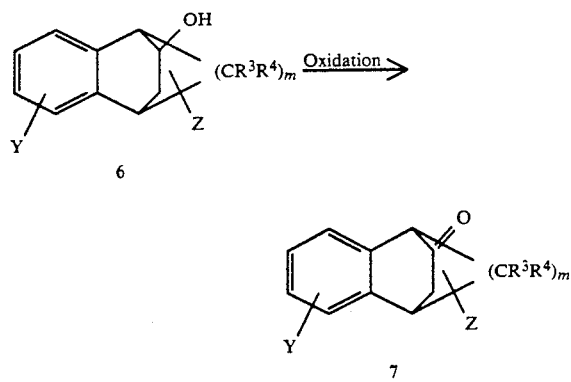

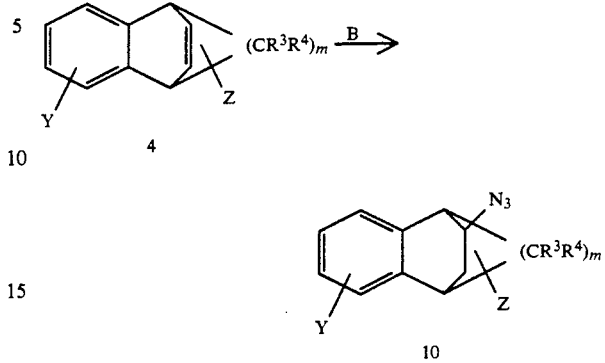

wherein m, $R^3$, $R^4$, Y and Z are as defined previously.

In the fourth step of the process, the alcohol 6 is oxidized to the ketone 7 employing oxidizing agents such as pyridinium chlorochromate, chromium trioxide, potassium dichromate, or other oxidizing agents familiar to those skilled in the art. This oxidation can be achieved in either aqueous or organic solvents, depending on the oxidizing agent of choice, and at temperatures ranging from $-60°$ C. to reflux of the reaction mixture.

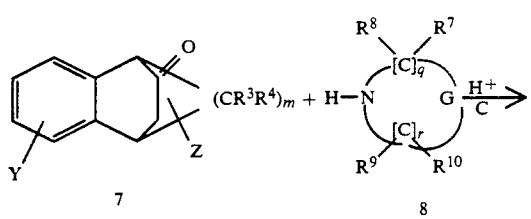

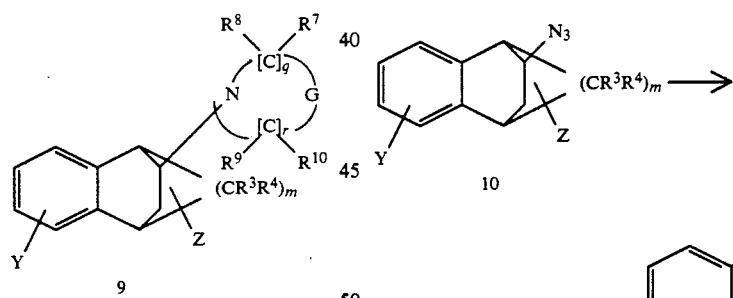

wherein G, Y, Z, m, q, r, $R^3$, $R^4$ and $R^7$ through $R^{10}$ are as defined previously; wherein C is a reducing agent such as sodium cyanoborohydride or sodium borohydride.

In the fifth step of the process, the ketone 7 is converted to the amine 9 by mixing 7 with the amine 8 where G, q, r, and $R^7$ through $R^{10}$ are as previously defined. The reagents are mixed in the presence of an acid catalyst such as p-toluenesulfonic acid, trifluoroacetic acid, or acetic acid and with a reducing agent C in a solvent such as ethanol, methanol, or ethyl acetate. The reducing agent C can be a reagent such as sodium cyanoborohydride, sodium borohydride or another reducing agent familiar to those skilled in the art. The temperature of the reaction may vary from room temperature to reflux of the reaction mixture.

wherein m, $R^3$, $R^4$, Y and Z are as defined previously.

An alternate process that can be used to synthesize the products of the invention starts with the diene 4 as described in Generic Procedure I where m, $R^3$, $R^4$, Y and Z are previously described. The diene 4 is combined with sodium azide in a solvent or a mixture of solvents such as ethanol, methanol, toluene or water and with a metallic catalyst such as mercuric acetate. The temperature of the reaction can vary from room temperature to reflux of the reaction mixture. The reaction mixture is then treated with a reducing agent such as sodium borohydride, sodium cyanoborohydride, or other reducing agents familiar to those skilled in the art and the temperature of the reduction can vary from room temperature to about 50° C.

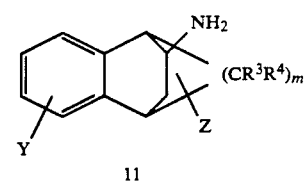

wherein m, $R^3$, $R^4$, Y and Z are as defined previously.

In the second step of the process, azides of general structure 10 are converted to amines of general structure 11 by reaction with a reducing agent such as lithium aluminum hydride, sodium borohydride, hydrogen in the presence of a catalyst, or a variety of other reducing systems familiar to those skilled in the art. The reagents are combined in a solvent such as ether, tetrahydrofuran, ethanol, or methanol and the reaction temperature can vary from room temperature to reflux of the reaction mixture.

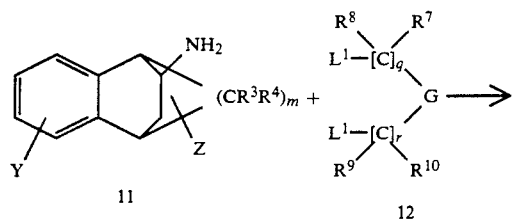
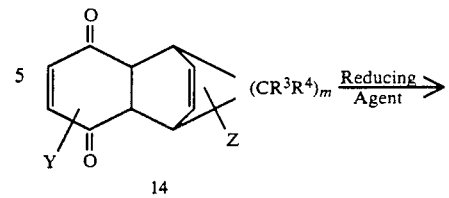

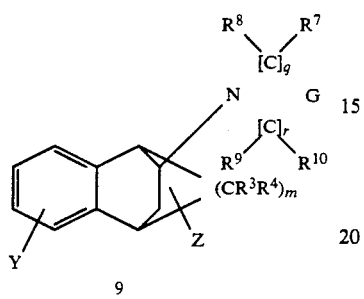

wherein G, Y, Z, m, q, r, $R^3$, $R^4$ and $R^7$ through $R^{10}$ are as defined previously; wherein $L^1$ represents a good leaving group such as chloro, bromo, mesyl, or tosyl.

In the third step of the process, amines of general structure 9 are prepared by combining amines of general structure 11 with compounds of general structure 12 where G, q, r, and $R^7$ through $R^{10}$ are as defined previously and $L^1$ represents a good leaving group such as chloro, bromo, mesyl or tosyl. The compounds can be combined in a variety of solvents such as toluene, dimethylformamide, acetonitrile or ethanol. The temperature of the reaction can vary from room temperature to reflux of the reaction mixture.

Generic Procedure III

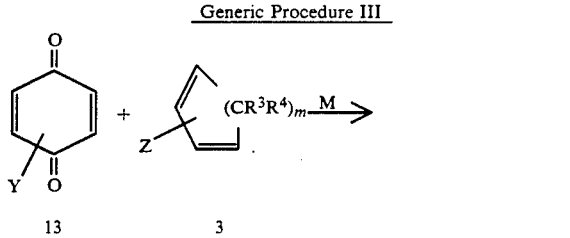

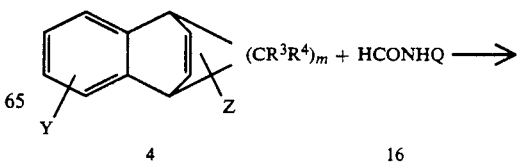

wherein m, $R^3$, $R^4$, Y and Z are as defined previously.

A third process that can be used to synthesize the products of the invention starts with quinones of general structure 13 where Y has the value assigned previously. The quinone is combined with the diene 3 where m, $R^3$, $R^4$ and Z have the values assigned previously. The reaction is best achieved by mixing the reagents in a solvent like tetrahydrofuran, toluene or benzene. The temperature of the reaction can vary from room temperature to reflux of the reaction mixture.

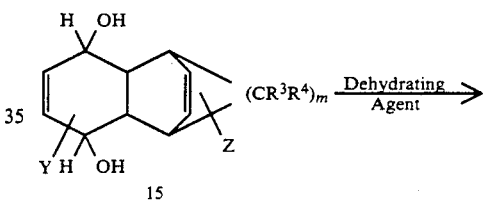

wherein m, $R^3$, $R^4$, Y and Z are as defined previously.

In the second step of the process, the bicyclic quinone 14 is reduced to the diol 15 by mixing the quinone 14 with a reducing agent such as lithium aluminum hydride or diisobutylaluminum hydride in a solvent such as ether or tetrahydrofuran. The temperature of the reaction mixture can vary from room temperature to reflux of the reaction mixture.

wherein m, $R^3$, $R^4$, Y and Z are as defined previously.

In the third step of the process, the diol 15 is dehydrated to the diene 4 by mixing the diol 15 with a dehydrating agent such as phosphorous oxychloride, phosphorous pentachloride or other dehydrating agents familiar to those skilled in the art. The reaction is best achieved by mixing the reagents in a solvent such as ether, tetrahydrofuran, or pyridine and at a temperature which can vary from 0° C. to reflux of the reaction mixture.

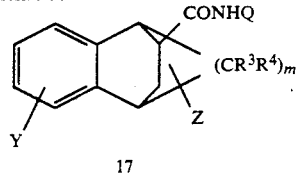

17 wherein m, $R^3$, $R^4$, Y and Z are as defined previously; wherein Q represents a group such as lower alkyl or phenyl.

In the fourth step of the process, the diene 4 is combined with a formamide 16 and a free radical generator such as benzoyl peroxide or m-chloroperbenzoic acid. The reagents are combined neat or in a solvent such as toluene or benzene. The reaction temperature can vary from room temperature to about 160° C.

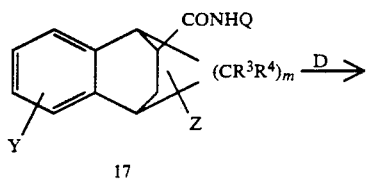

17

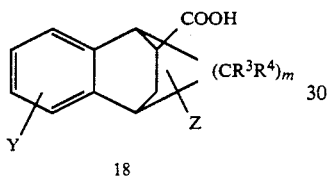

18 wherein m, $R^3$, $R^4$, Y and Z are as defined previously; wherein Q represents a group such as lower alkyl or phenyl; wherein D is selected from a variety of bases such as sodium hydroxide, lithium hydroxide or potassium hydroxide.

In the fifth step of the process, the amide 17 is hydrolyzed to the acid 18 by mixing the amide with water in the presence of a base such as sodium hydroxide, lithium hydroxide, or potassium hydroxide. The reaction is best achieved by mixing the reagents neat or in a solvent such as ethanol or methanol. The reaction temperature can vary from about room temperature to reflux of the reaction mixture.

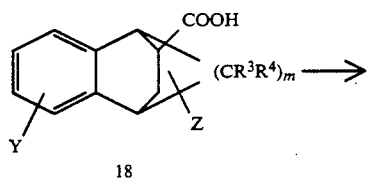

18

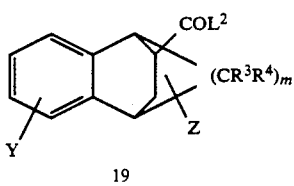

19 wherein m, $R^3$, $R^4$, Y and Z are as defined previously; wherein $L^2$ represents a good leaving group such as chloro, bromo, or acyl.

In the sixth step of the process, the acid 18 is converted to a compound of general structure 19 where $L^2$ is a good leaving group such as chloro, bromo, or acyl.

The conversion can be best achieved by mixing the acid 18 with reagents such as thionyl chloride, phosphorous oxychloride, phosphorous tribromide, diethylcyanophosphonate or other reagents. This conversion is best achieved by mixing the reagents neat or in an aprotic solvent such as tetrahydrofuran, methylene chloride, dimethylformamide or ether. The temperature of the reaction can vary from room temperature to reflux of the reaction mixture.

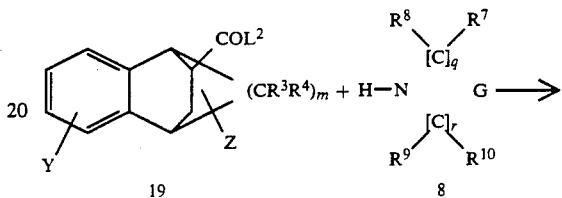

19     8

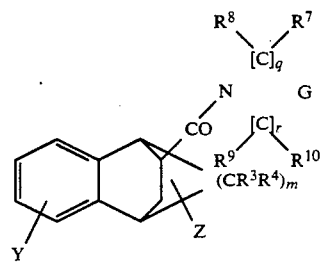

20 wherein Y, Z, $L^2$, G, m, q, r, $R^3$, $R^4$, and $R^7$ through $R^{10}$ are as previously defined.

In the seventh step of the process, compounds of general structure 19 are converted to amides of general structure 20 by reaction with amines of general structure 8, where G, q, r, and $R^7$ through $R^{10}$ are as defined before. The conversion is best achieved by mixing the reagents neat or in an aprotic solvent such as tetrahydrofuran, ether, or methylene chloride. The temperature of the reaction can vary from about 0° C. to reflux of the reaction mixture.

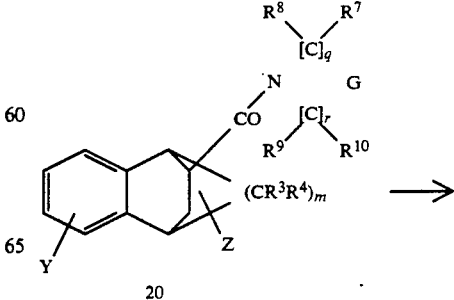

20

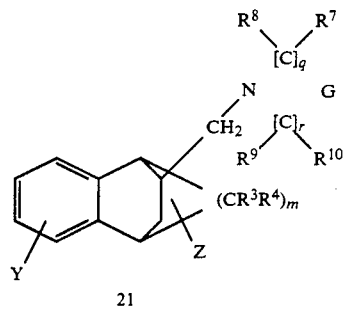

21 wherein Y, Z, $L^2$, G, m, q, r, $R^3$, $R^4$, and $R^7$ through $R^{10}$ are as previously defined.

In the seventh step of the process, amides of general structure 20 are converted to amines of general structure 21 by employing reducing agents such as lithium aluminum hydride, sodium cyanoborohydride, sodium borohydride, or other reducing agents familiar to those skilled in the art. This reduction can be accomplished in either protic or aprotic solvents, depending on the reducing agent of choice, and at temperatures ranging from room temperature to reflux of the reaction mixture.

The following Examples I–XVI are detailed descriptions of the methods of preparation of compounds of Formula I–III. These detailed preparations fall within the scope of, and serve to exemplify, the above described Generic Procedures which form part of the invention. These Examples I–XVI are presented for illustrative purposes only and are not intended as a restriction on the scope of the invention. All parts are by weight unless otherwise indicated. Most of the commercially available starting materials were obtained from Aldrich Chemical Company, Milwaukee, Wisc.

EXAMPLE I

Tricyclo[6.2.2.0]dodeca-4,9-diene-3,6-dione

Quinone (20 g) was combined with benzene (160 ml) and 1,3-cyclohexadiene (50 g) and stirred for 2 days at room temperature. The solution was concentrated on a rotary evaporator and the residue was recrystallized from ethanol to provide the product as a yellow solid.

EXAMPLE II

Tricyclo[6.2.2.0]dodeca-4,9-diene-3,6-diol

Tricyclo[6.2.2.0]dodeca-4,9-diene-3,6-dione (2.55 g) was combined with toluene (500 ml) and 1M diisobutylaluminum hydride in tetrahydrofuran (30 ml) and the mixture was stirred at room temperature for 3 hours. The solution was cooled in an ice bath and 30% potassium hydroxide solution was added. The resulting mixture was stirred for 30 minutes and the layers separated. The aqueous layer was extracted with ether (2×100 ml) and the combined organic layers were concentrated on a rotary evaporator. The residue was recrystallized from hexane/ethyl acetate to provide the product as a white solid.

EXAMPLE III

Benzobicyclo[2.2.2]octadiene

Tricyclo[6.2.2.0]dodeca-4,9-diene-3,6-diol (3.08 g) was combined with pyridine (30 ml) and cooled to 0° C. Phosphorous oxychloride (6.6 ml) was added to the cold solution and the mixture stirred for 3 days at room temperature. The resulting mixture was heated on a steam bath for 1 hour, cooled in an ice bath, and treated with ice (200 g). The resulting mixture was extracted with hexane (5×100 ml) and the combined hexane layers were washed with water (2×50 ml), 6N Hydrochloric acid (2×50 ml), and water (2×50 ml). The organic solution was dried over magnesium sulfate and concentrated on a rotary evaporator. The residue was distilled on a Kugelrohr apparatus (60° C. at 5 mm Hg) to provide the product as a colorless liquid.

EXAMPLE IV

2-Benzobicyclo[2.2.2]octeneone

A solution of mercuric acetate (3 g) in water (30 ml) was treated with a solution of benzobicyclo[2.2.2]octadiene (1.5 g) in tetrahydrofuran (30 ml) and the resulting mixture was stirred at room temperature for 24 hours. The solution was treated with a solution of 10% sodium hydroxide in water (30 ml), followed by sodium borohydride (3 g). The resulting mixture was stirred for 30 minutes and the resulting layers were separated. The aqueous layer was extracted with ether (2×30 ml) and the combined organic layers were concentrated on a rotary evaporator. The residue was combined with methylene chloride (25 ml) and pyridinium chlorochromate (0.5 g) and the solution was stirred at room temperature for 4 hours. The solution was washed with water (30 ml) and the organic layer was dried over magnesium sulfate. The solvent was removed on a rotary evaporator and the product was purified by preparative centrifugally accelerated radial thin layer chromatography using 15% ethyl acetate in hexane as the eluant. After removal of the eluant on a rotary evaporator, the product was obtained as a yellow oil.

EXAMPLE V 1-(2-Benzobicyclo[2.2.2]octenyl)piperidine (Compound No. 1)

2-Benzobicyclo[2.2.2]octeneone (0.8 g) was combined with piperidine (3 ml), p-toluenesulfonic acid (0.1 g), and toluene (20 ml) and heated to reflux for 20 hours. The solution was concentrated on a rotary evaporator and the residue was combined with glacial acetic acid (20 ml) and sodium cyanoborohydride (0.6 g) and stirred at room temperature for 6 hours. The solution was made basic by the addition of 10% sodium hydroxide in water. The resulting mixture was were dried over magnesium sulfate and concentrated on a rotary evaporator. The residue was distilled on a Kugelrohr apparatus (120° C. at 0.05 mm Hg) to provide the product as a colorless oil. Analytical data are reported in Table I.

EXAMPLE VI

2-Benzobicyclo[2.2.2]octenecarboxylic acid

Benzobicyclo[2.2.2]octadiene (0.5 g) was combined with t.-butylformamide (5 ml) and t. butylperoxide (0.3 ml) and heated to 160° C. for 6 hours. The mixture was dissolved in ether (50 ml), treated with charcoal, and filtered. The solvent was removed on a rotary evaporator and the residue was distilled on a Kugelrohr apparatus (120° C. at 0.05 mm Hg) to provide an orange solid which solidified upon standing. The solid was combined with concentrated sulfuric acid (0.5 ml), concentrated hydrochloric acid (25 ml) and ethanol (25 ml). The mixture was heated to reflux for 12 hours, cooled to room temperature, and treated with water (50 ml). The mixture was extracted with ether (3×25 ml) and the combined ether layers were extracted with 5% sodium hydroxide in water (3×25 ml). The combined basic solutions were made acidic with concentrated hydrochloric acid and the mixture was extracted with ether (3×30 ml). The combined ether layers were dried over magnesium sulfate and the solvent was removed on a rotary evaporator to provide the product as a white solid.

EXAMPLE VII 1-(2-Benzobicyclo[2.2.2]octenyl)methylpiperidine Compound No. 2)

2-Benzobicyclo[2.2.2]octenecarboxylic acid (0.02 g) was combined with piperidine (0.5 ml), diethylcyanophosphonate (0.5 ml), triethylamine (1 ml) and dimethylformamide (15 ml) and stirred for 2 hours at room temperature. Water (15 ml) was added and the mixture was extracted with ether (3×15 ml). The combined ether solutions were washed with water (2×25 ml) and the ether solution was dried over magnesium sulfate and the ether removed on a rotary evaporator. The residue was combined with tetrahydrofuran (10 ml) and lithium aluminum hydride (0.2 g) and heated to reflux for 2 hours. The mixture was cooled in an ice bath, treated with ethanol (1 ml) and water (1 ml) and the solids were removed by filtration. The filtrate was concentrated on a rotary evaporator and the residue was distilled on a Kugelrohr apparatus (120° C. at 0.05 mm Hg) to provide the product as a colorless oil. Analytical data are reported in Table I.

EXAMPLE VIII 1-(2-Benzobicyclo[2.2.2]octenyl)methyl-4-methylpiperazine (Compound No. 3)

2-Benzobicyclo[2.2.2]octenecarboxylic acid (1 g) was combined with thionyl chloride (10 ml) and heated to reflux for 3 hours. The thionyl chloride was removed by distillation and the residue was dissolved in ether (10 ml). The ether solution was added dropwise to a solution of 1-methylpiperazine in ether (25 ml) and the mixture stirred at room temperature for 10 minutes. The solution was treated with 10% sodium hydroxide in water (10 ml) and the mixture stirred for 10 minutes. The layers were separated and the ether layer was dried over magnesium sulfate and concentrated on a rotary evaporator. The residue was combined with tetrahydrofuran (25 ml) and lithium aluminum hydride (0.5 g) and heated to reflux for 12 hours. The mixture was cooled, treated with water (1 ml) and filtered. The filtrate was concentrated on a rotary evaporator and the residue was combined with ether (25 ml). The ether solution was extracted with 6N hydrochloric acid (15 ml), the aqueous layer was made basic with 10% sodium hydroxide in water, and the resulting mixture was extracted with ether (3×25 ml). The combined ether layers were dried over magnesium sulfate and the solvent removed on a rotary evaporator. The residue was distilled on a Kugelrohr apparatus (120° C. at 0.05 mm Hg) to provide the product as a colorless oil. Analytical data are reported in Table I.

EXAMPLE IX

Benzobicyclo[2.2.1]heptadiene

1-Bromo-2-iodobenzene (1 ml) was combined with cyclopentadiene (1.5 ml) and added dropwise to a mixture of magnesium (0.25 g) and tetrahydrofuran (25 ml) which had been heated to reflux. After the addition, heating was continued for 1 hour. The mixture was cooled to room temperature, treated with water (50 ml), and extracted with ether (3×30 ml). The combined organic layers were dried over magnesium sulfate and the solvents removed on a rotary evaporator. The residue was distilled on a Kugelrohr apparatus (40° C. at 0.1 mm Hg) to provide the product as a yellow oil.

EXAMPLE X

2-Benzobicyclo[2.2.1]heptenecarboxylic acid

Benzobicyclo[2.2.2]octadiene (0.8 g) was combined with t.-butylformamide (5 ml) and t.-butylperoxide (1 ml) and heated to 150° C. for 4 hours. The solvent was removed on a rotary evaporator and the residue was combined with concentrated sulfuric acid (10 ml), glacial acetic acid (10 ml) and water (10 ml). The mixture was heated to 120° C. for 4 hours and cooled to room temperature. The mixture was extracted with ether (3×25 ml) and the combined ether layers were washed with water (2×25 ml) and extracted with 5% sodium hydroxide in water (3×25 ml). The combined basic solutions were made acidic with concentrated hydrochloric acid and the mixture was extracted with ether (3×30 ml). The combined ether layers were dried over magnesium sulfate and the solvent was removed on a rotary evaporator to provide the product as a yellow oil.

EXAMPLE XI 1-(2-Benzobicyclo[2.2.1]heptenyl)methylpiperidine (Compound No. 5)

2-Benzobicyclo[2.2.1]heptenecarboxylic acid (0.4 g) was combined with piperidine (1 ml), diethylcyanophosphonate (1 ml), triethylamine (2 ml) and dimethylformamide (10 ml) and stirred for 2 hours at room temperature. Water (15 ml) was added and the mixture was extracted with ether (3×15 ml). The combined ether solutions were washed with water (2×25 ml) and the ether solution was dried over magnesium sulfate and the ether removed on a rotary evaporator. The residue was combined with tetrahydrofuran (25 ml) and lithium aluminum hydride (0.2 g) and heated to reflux for 12 hours. The mixture was cooled in an ice bath, treated with ethanol (1 ml) and water (0.5 ml) and the solids were removed by filtration. The filtrate was concentrated on a rotary evaporator and the residue was dissolved in 6N HCl (20 ml). The acidic solution was washed with ether (2×25 ml) and the aqueous solution was made basic with 50% sodium hydroxide solution. The mixture was extracted with ether (3×25 ml) and the combined ether solutions were dried over magnesium sulfate and the ether removed on a rotary evaporator. The residue was distilled on a Kugelrohr apparatus (80° C. at 0.05 mm Hg) to provide the product as a colorless oil. Analytical data are reported in Table I.

EXAMPLE XII

2-Benzobicyclo[2.2.1]heptenone

A solution of mercuric acetate (4 g) in water (10 ml) was treated with a solution of benzobicyclo[2.2.1]heptadiene (2 g) in tetrahydrofuran (25 ml) and the resulting mixture was stirred at room temperature for 24 hours. The solution was treated with a solution of 10% sodium hydroxide in water (5 ml), followed by sodium borohydride (0.5 g). The resulting mixture was stirred for 30 minutes and the resulting layers were separated. The aqueous layer was extracted with ether (2×30 ml) and the combined organic layers were dried over magnesium sulfate and concentrated on a rotary evaporator. The residue was combined with methylene chloride (25 ml) and pyridinium chlorochromate (3 g) and the solution was stirred at room temperature for 12 hours. The solution was washed with water (30 ml) and the organic layer was dried over magnesium sulfate. The solvent was removed on a rotary evaporator and the product was purified by preparative centrifugally accelerated radial thin layer chromatography using 25% ethyl acetate in hexane as the eluant. After removal of the eluant on a rotary evaporator, the product was obtained as a yellow oil.

EXAMPLE XIII 1-(2-Benzobicyclo[2.2.1]heptenyl)piperidine (Compound No. 6)

2-Benzobicyclo[2.2.1]hepteneone (0.5 g) was combined with piperidine (1 ml), p-toluenesulfonic acid (0.1 g), and toluene (25 ml) and heated to reflux for 20 hours. The solution was concentrated on a rotary evaporator and the residue was distilled on a Kugelrohr apparatus (120° C. at 0.05 mm Hg). The distillate was combined with glacial acetic acid (10 ml) and sodium cyanoborohydride (0.5 g) and stirred at room temperature for 12 hours. The solution was made basic by the addition of 10% sodium hydroxide in water. The resulting mixture was extracted with ether (3×50 ml) and the combined ether layers were dried over magnesium sulfate and concentrated on a rotary evaporator. The residue was distilled on a Kugelrohr apparatus (120° C. at 0.05 mm Hg) to provide the product as a colorless oil. Analytical data are reported in Table I.

EXAMPLE XV

2-Aminobenzobicyclo[2.2.1]heptene

Sodium azide (2 g) was combined with water (40 ml) and tetrahydrofuran (40 ml) and cooled to 0° C. Mercuric acetate (4g) was added to the cold solution and the mixture was stirred for 20 minutes. Benzobicyclo[2.2.1]heptadiene (2 g) was added to the stirred mixture and the resulting mixture was heated to 75° C. for 24 hours. The solution was cooled to room temperature, treated with 10% sodium hydroxide in water (10 ml) and sodium borohydride (0.4 g), and stirred for 1 hour. The two layers were separated and the organic layer was dried over magnesium sulfate and the solvent removed on a rotary evaporator. The residue was combined with tetrahydrofuran (20 ml) and added to a suspension of lithium aluminum hydride (0.1 g) in tetrahydrofuran (20 ml). The mixture was stirred at room temperature for 3 hours, treated with water (1 ml) and filtered. The solvent was removed on a rotary evaporator to provide the product as a yellow oil.

EXAMPLE XVI 1-(2-Benzobicyclo[2.2.1]heptenyl)-4-methylpiperazine (Compound No. 8)

2-Aminobenzobicyclo[2.2.1]heptene (1.1 g) was combined with mechlorethamine hydrochloride (1.4 g), potassium carbonate (1.5 g), and acetonitrile (25 ml) and heated to reflux for 24 hours. Water (50 ml) was added to the mixture and the resulting mixture was extracted with ether (3×50 ml). The combined ether solutions were dried over magnesium sulfate and the ether was removed on a rotary evaporator. The residue was combined with concentrated hydrochloric acid (5 ml) and 2-propanol (25 ml) and the solvent was removed on a rotary evaporator. The residue was suspended in 2-propanol and the solvent was removed on a rotary evaporator. This latter step was repeated. The residue was recrystallized from 2-propanol to provide the product as a tan solid. Analytical data are reported in Table I.

Table I is a list of 8 specific compounds of most interest within Formula I. The preparation of representative compounds from Table I is described in detail in Example Procedures I-XVI, above.

TABLE I

| Compound No. | Name | Structure | Method of Preparation | Elemental Theor. | | Analysis Found |
|---|---|---|---|---|---|---|
| 1 | 1-(2-benzobicyclo[2.2.2]octenyl)piperidine.0.1H$_2$O | 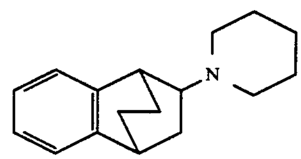 | I-V | C | 83.96 | 83.65 |
| | | | | H | 9.61 | 9.42 |
| | | | | N | 5.75 | 5.36 |
| 2 | 1-(2-benzobicyclo[2.2.2]octenyl)methylpiperidine .0.14H$_2$O | 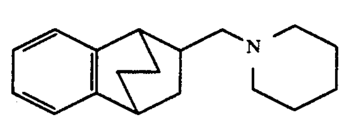 | I-III,VI,VII | C | 83.81 | 83.85 |
| | | | | H | 9.88 | 10.16 |
| | | | | N | 5.40 | 4.88 |
| 3 | 1-(2-benzobicyclo[2.2.2]octenyl)methyl-4-methyl-piperazine.0.1H$_2$O | 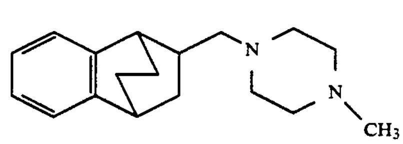 | I-III,VI,VIII | C | 79.42 | 79.48 |
| | | | | H | 9.70 | 9.68 |
| | | | | N | 10.29 | 10.20 |

TABLE I-continued

| Compound No. | Name | Structure | Method of Preparation | Elemental Theor. | | Analysis Found |
|---|---|---|---|---|---|---|
| 4 | 1-(2-benzobicyclo[2.2.2] octenyl)-4-methylpiperazine .0.4Et₂O | 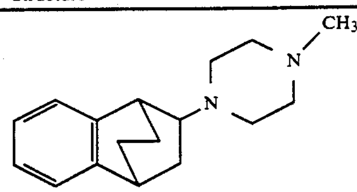 | I-V | C | 78.97 | 79.00 |
| | | | | H | 9.24 | 9.00 |
| | | | | N | 9.94 | 9.58 |
| 5 | 1-(2-benzobicyclo- [2.2.1.]heptenyl) methylpiperidine | 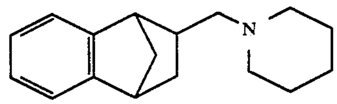 | IX-XI | C | 84.59 | 84.40 |
| | | | | H | 9.60 | 9.82 |
| | | | | N | 5.80 | 5.81 |
| 6 | 1-(2-benzobicyclo- [2.2.1]heptenyl)piper- idine | 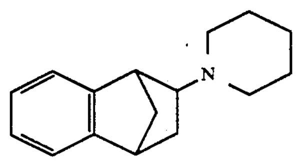 | IX,XII,XIII | C | 83.21 | 83.27 |
| | | | | H | 9.33 | 9.16 |
| | | | | N | 6.06 | 5.74 |
| 7 | 1-(2-benzobicyclo[2.2.1]- heptenyl)methyl-4- methylpiperazine.2HCl | 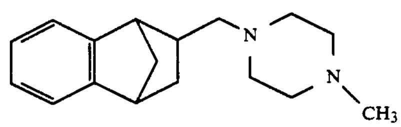 | IX,X,XIV | C | 59.58 | 59.65 |
| | | | | H | 8.11 | 8.11 |
| | | | | N | 8.17 | 7.66 |
| 8 | 1-(2-benzobicyclo[2.2.1]- 4-methylpiperazine.2HCl.2.7H₂O | 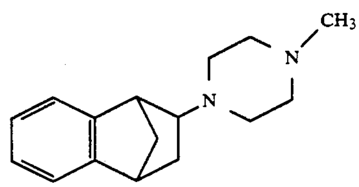 | IX,XV,XVI | C | 52.07 | 51.99 |
| | | | | H | 8.08 | 8.08 |
| | | | | N | 7.59 | 8.17 |

Biological Evaluation

Radioreceptor Assay

Compounds 1-8 were compared against di-o-tolyl-guanidine (DTG) [E. Weber et al, *Proc. Natl. Acad. Sci.*, 83, 8784-8788, 1986] to determine the relative potency of the compounds interacting with the sigma receptor. To determine the effects of the compounds in a sigma receptor assay, crude membrane preparations were prepared as follows. Brains from male Sprague-Dawley rats were homogenized in 10 volumes (wt/vol) of 0.32M sucrose, using a Polytron grinder. The homogenate was centrifuged at 900×g for 10 minutes at 4° C. The supernatant was collected and centrifuged at 22,000×X g for 20 minutes at 4° C. The pellet was resuspended in 10 volumes of 50 mM Tris/HCl buffer (pH 7.4) and centrifuged at 22,000×g for 20 minutes at 4° C. The pellet was resuspended in 5 mM Tris/HCl buffer (pH 7.4) to give a final concentration of 250 mg/ml of the crude material. Incubation tubes were prepared in triplicate and contained 0.1 ml of tissue suspension, 2 nM of [³H]-(+)-1-propyl-3-(3-hydroxy-phenyl)piperidine [³H]-3-(+)-PPP, and varying concentrations of the displacing ligand (0.1-1000 nM) in a final volume of 0.5 ml. After a 1 hr incubation at room temperature, the contents of the test tubes were filtered through GS filter paper which had been presoaked for at least 2 hours in 0.05% polyethyleneimine. The test tubes were rinsed three times with Tris/HCl buffer. Radioactivity on the filters was determined using liquid scintillation spectrometry and inhibition curves were calculated according to the method of Cheng and Prusoff [*Biochem. Pharmacol.*, 22, 3099-3108 (1973)].

TABLE II

| Test Compound | Ki apparent (nM) (units ± SEM) |
|---|---|
| DTG | 47 ± 5 |
| Compound No. 1 | 137 ± 9 |
| Compound No. 2 | 11 ± 6 |
| Compound No. 3 | 4 ± 2 |
| Compound No. 4 | 170 ± 40 |
| Compound No. 5 | 9 ± 4 |
| Compound No. 6 | 0.075 ± 0.06 |
| Compound No. 7 | 22000 ± 2000 |
| Compound No. 8 | 943 ± 3 |

Blockade of Agonist-induced Stereotyped Behavior and Ataxia

Compounds of the invention were evaluated for their ability to block the effects of N-allylnormetazocine on the induction of stereotyped behavior and ataxia. To test for antagonism, drugs are administered at varying times before i.p. administration of 15 mg/kg of N-allylnormetazocine. Behavioral and ataxia ratings are taken at 2.5 minutes, 5 minutes, and every 5 minutes thereafter until the animal returns to control behavior. The rating scale for stereotyped behavior is: (0) inactive or in-place non-repetitive activity; (1) sniffing, grooming, or rearing; (2) undirected head movements, reciprocal forepaw treading or a greater frequency of sniffing than in (1); (3) appearance of circling, weaving or backward walking; (4) gagging or continuous circling, weaving or backward walking; and (5) dyskinetic extension or flexation of head, neck and limbs, or rapid and continuous weaving greater than (4). The rating scale for ataxia is: (0) inactive or coordinated movements; (1) awkward or jerky movements or loss of balance while rearing; (2) stumbles or awkward position; (3) falling or leaning against cage; (4) supports weight on stomach or haunches; and (5) unable to move except for twitching movements. The lowest dose of the test compound which is capable of blocking the stereotyped behavior and ataxia induced by N-allylnormetazocine was determined. For example, at a dose of 1 mg/kg i.p., Compound No. 3 and Compound No. 5 fully blocked N-allylnormetazocine-induced stereotyped behavior. At a dose of 3 mg/kg Compound No. 2 fully blocked N-allylnormetazocine-induced stereotyped behavior, while Compound No. 6 blocked these same responses at 10 mg/kg.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

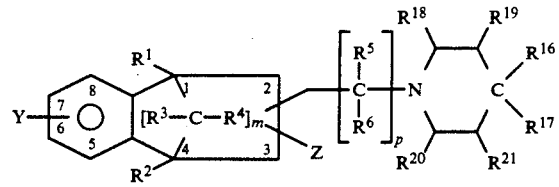

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^5$ and $R^6$ is independently selected from hydrido, alkyl, fluoroalkyl, benzyl and phenyl;

wherein each of $R^{16}$ through $R^{21}$ is independently selected from hydrido, hydroxy, alkyl, benzyl, phenyl, alkoxy, fluoroalkyl and fluoro;

wherein any foregoing alkyl radical, alone or within another radical, is selected from alkyl radicals of one to ten carbon atoms;

wherein m is one or two; wherein p is zero or one; or a pharmaceutically-acceptable salt thereof.

2. Compound of claim 1 wherein each of $R^1$, $R^2$, $R^3$, $R^4$, Y and Z is independently selected from hydrido, alkyl, halo and haloalkyl; wherein each $R^5$, $R^6$ and $R^{16}$ through $R^{21}$ is independently selected from hydrido, alkyl, benzyl and phenyl; wherein m is one or two; wherein p is zero or one; or a pharmaceutically-acceptable salt thereof.

3. Compound of claim 2 selected from compounds, or a pharmaceutically-acceptable salt thereof, of the group consisting of
1-(2-benzobicyclo[2.2.2]octenyl)methylpiperidine; 1-(2-benzobicyclo[2.2.2]octenyl)piperidine; 1-(2-benzobicyclo[2.2.1]heptenyl)methylpiperidine; and 1-(2-benzobicyclo[2.2.1]heptenyl)piperidine.

4. A pharmaceutical composition comprising a therapeutically-effective amount of an active compound for treating or preventing a psychotic disorder, a convulsive disorder, a dystonic disorder or cerebral ischemia, and a pharmaceutically-acceptable carrier or diluent, said active compound selected from a family of compounds of the formula

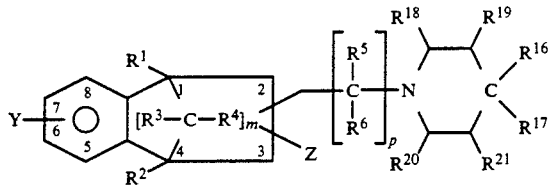

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^5$ and $R^6$ is independently selected from hydrido, alkyl, fluoroalkyl, benzyl and phenyl;
wherein each of $R^{16}$ through $R^{21}$ is independently selected from hydrido, hydroxy, alkyl, benzyl, phenyl, alkoxy, fluoroalkyl and fluoro;
wherein any foregoing alkyl radical, alone or within another radical, is selected from alkyl radicals of one to ten carbon atoms;
wherein m is one or two; wherein p is zero or one; or a pharmaceutically-acceptable salt thereof.

5. The composition of claim 4 wherein each of $R^1$, $R^2$, $R^3$, $R^4$, Y and Z is independently selected from hydrido, alkyl, halo and haloalkyl; wherein each $R^5$, $R^6$ and $R^{16}$ through $R^{21}$ is independently selected from hydrido, alkyl, benzyl and phenyl; wherein m is one or two; wherein p is zero or one; or a pharmaceutically-acceptable salt thereof.

6. The composition of claim 5 wherein said active compound is selected from compounds, or a pharmaceutically-acceptable salt thereof, of the group consisting of
1-(2-benzobicyclo[2.2.2]octenyl)methylpiperidine; 1-(2-benzobicyclo[2.2.2]octenyl)piperidine; 1-(2-benzobicyclo[2.2.1]heptenyl)methylpiperidine; and 1-(2-benzobicyclo[2.2.1]heptenyl)piperidine.

7. A method for treating a patient afflicted with or susceptible to a psychotic disorder, a convulsive disorder, dystonia or cerebral ischemia, which method comprises administering to the patient a therapeutically-effective amount of a compound of the formula

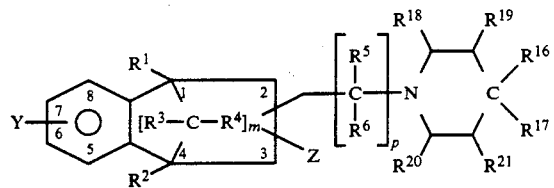

wherein each of $R^1$, $R^2$, $R^3$, $R^4$, Y and Z is independently selected from hydrido, hydroxy, alkyl, benzyl, phenyl, alkoxy, halo and haloalkyl; wherein each of $R^5$ and $R^6$ is independently selected from hydrido, alkyl, fluoroalkyl, benzyl and phenyl;
wherein each of $R^{16}$ through $R^{21}$ is independently selected from hydrido, hydroxy, alkyl, benzyl, phenyl, alkoxy, fluoroalkyl and fluoro;
wherein any foregoing alkyl radical, alone or within another radical, is selected from alkyl radicals of one to ten carbon atoms;
wherein m is one or two; wherein p is zero or one; or a pharmaceutically-acceptable salt thereof.

8. The method of claim 7 wherein each of $R^1$, $R^2$, $R^3$, $R^4$, Y and Z is independently selected from hydrido, alkyl, halo and haloalkyl; wherein each of $R^5$, $R^6$ and $R^{16}$ through $R^{21}$ is independently selected from hydrido, alkyl, benzyl and phenyl; wherein m is two; wherein p is zero or one; or a pharmaceutically-acceptable salt thereof.

9. The method of claim 8 wherein said compound is selected from compounds, or a pharmaceutically-acceptable salt thereof, of the group consisting of
1-(2-benzobicyclo[2.2.2]octenyl)methylpiperidine; 1-(2-benzobicyclo[2.2.2]octenyl)piperidine; 1-(2-benzobicyclo[2.2.1]heptenyl)methylpiperidine; and 1-(2-benzobicyclo[2.2.1]heptenyl)piperidine.

10. The method of claim 7 for treating cerebral ischemia.

11. The method of claim 7 for treating a psychotic disorder.

12. The method of claim 7 for treating a psychotic disorder.

13. The method of claim 7 for treating dystonia.

* * * * *